United States Patent
LaMee

(10) Patent No.: US 8,475,166 B1
(45) Date of Patent: Jul. 2, 2013

(54) UPPER DENTURE RELEASE APPARATUS AND METHOD OF USE

(76) Inventor: Maurice LaMee, Ormond Beach, FL (US)

( * ) Notice: Subject to any disclaimer, the term of this patent is extended or adjusted under 35 U.S.C. 154(b) by 0 days.

(21) Appl. No.: 13/517,715

(22) Filed: Jun. 14, 2012

(51) Int. Cl.
   *A61C 3/00* (2006.01)
(52) U.S. Cl.
   USPC ............................................. 433/141
(58) Field of Classification Search
   USPC ................................. 433/1–3, 141
   See application file for complete search history.

(56) References Cited

U.S. PATENT DOCUMENTS

| | | | |
|---|---|---|---|
| 2,315,660 A * | 4/1943 | Sahr | 433/44 |
| 2,341,155 A * | 2/1944 | Myerson | 433/41 |
| 3,401,457 A * | 9/1968 | Hickham | 433/5 |
| 3,579,834 A | 5/1971 | Reed, Jr. | |
| 4,102,375 A * | 7/1978 | Rossini | 81/30 |
| 4,609,353 A | 9/1986 | Kline | |
| 4,627,817 A | 12/1986 | Higa | |
| 4,815,972 A * | 3/1989 | Howe | 433/5 |
| 5,197,877 A | 3/1993 | Andrew | |
| 5,197,878 A | 3/1993 | Lukase et al. | |
| 5,599,186 A | 2/1997 | Andrew | |
| 5,833,460 A | 11/1998 | Maeda | |
| 8,182,266 B2 * | 5/2012 | Creasman et al. | 433/141 |
| 2005/0064358 A1 * | 3/2005 | Nicozisis | 433/3 |
| 2006/0075606 A1 * | 4/2006 | Lawless | 16/430 |
| 2007/0209488 A1 * | 9/2007 | Nogueras | 81/489 |
| 2012/0009542 A1 * | 1/2012 | Keddington et al. | 433/75 |

* cited by examiner

*Primary Examiner* — Robyn Doan
*Assistant Examiner* — Matthew Nelson
(74) *Attorney, Agent, or Firm* — Allen, Dyer, Doppelt, Milbrath & Gilchrist, P.A.

(57) ABSTRACT

An upper denture release apparatus and method of use. A denture puller has a chin rest, arm attached to the chin rest, and a hook attached to an end of the arm opposite the chin rest. An upper denture has a notch sized and located to admit the hook when a wearer's chin rests on the chin rest. The method includes the steps of resting a wearer's chin on the chin rest, inserting the hook into the upper denture notch, and opening the wearer's mouth, thus pulling the upper denture off the wearer's upper gum. Arm length adjustment is shown, whereby the denture puller may be adjusted to fit differently-sized upper denture wearers. Preferred hook declination, hook toe, arm and notch floor angles are disclosed.

6 Claims, 6 Drawing Sheets

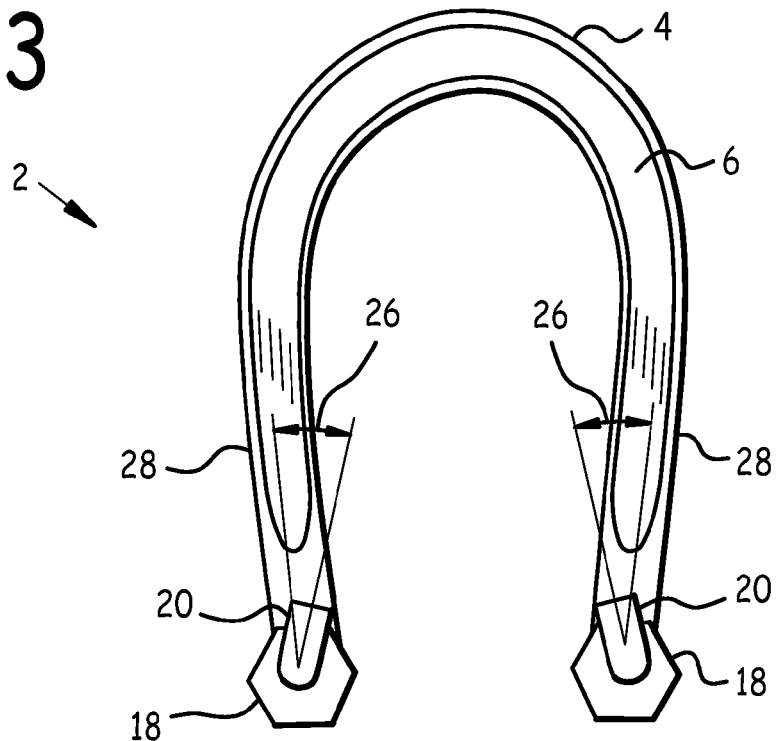
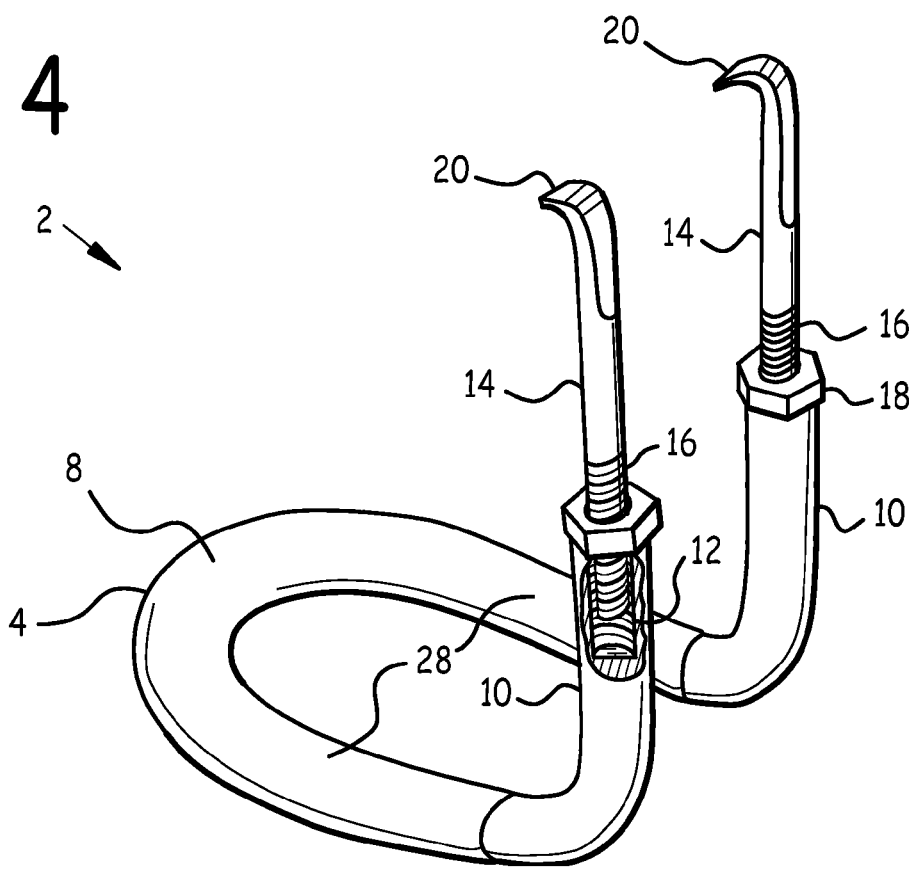

VII-VII

UPPER DENTURE RELEASE APPARATUS AND METHOD OF USE

BACKGROUND OF THE INVENTION

1. Field of the Invention

This invention relates to dentures, and in particular to an upper denture release apparatus and method of use.

2. Background of the Invention

Dentures, also referred to as false teeth, are used to replace missing teeth, which may include all upper or lower teeth. Loss of teeth necessitating use of a denture may be due to a variety of causes including dental disease such as periodontal disease or tooth decay. Other causes of tooth loss include malnutrition, dentinogenesis imperfecta, trauma, or drug use.

Modern dentures are held in place primarily by suction between the denture and the surface of the underlying gum. It is therefore important that the border seal around the perimeter of the denture to the underlying gum be continuous around its complete length so as to preserve the suction between the denture and the gum.

Dentures are also retained in place by means of implant posts which are implanted into the underlying bone. Color-coded rubber O-rings of differing stiffnesses are installed on the distal ends of the implant posts, and affect the strength of the friction fit between the denture and implant posts. A delicate balance must be achieved between the denture/implant fit being so tight as to render removal of the denture excessively difficult, and the denture/implant fit being too loose and not properly retaining the denture in position. Even where the correct balance is struck, it can be difficult to remove upper dentures for cleaning, sleeping, etc., especially where the individual is arthritic, or suffers from some other debilitating condition of the hands.

Where a denture is manufactured to replace upper teeth, the denture is referred to as an upper denture. It would be desirable to provide an apparatus and method to facilitate the removal of upper dentures.

EXISTING DESIGNS

A number of devices have been proposed to facilitate the removal of dentures. These are generally complex and hence difficult to use, and expensive. Therefore, it would be desirable to provide an apparatus and method to release upper dentures which is simple and easy to operate.

SUMMARY OF THE INVENTION

Accordingly, it is an object of the present invention to provide an upper denture release apparatus and method of use which is simple and effective to use. Design features allowing this object to be accomplished include a denture puller having an arm attached to a leg, a hook attached to an end of the arm, and a chin rest attached to the leg; and an upper denture having a notch sized to admit the hook. Advantages associated with the accomplishment of this object include faster and easier upper denture removal, even when the denture wearer suffers from arthritis.

It is another object of the present invention to provide an upper denture release apparatus and method of use which is adjustable in order to accommodate different denture wearer face sizes. Design features allowing this object to be accomplished include a denture puller having an arm attached to a leg, a hook attached to an end of the arm, arm length adjustment means, and a chin rest attached to the leg; and an upper denture having a notch sized to admit the hook. A benefit associated with the accomplishment of this object is the flexibility of application of the denture puller to different denture wearers' faces.

It is still another object of this invention to provide an upper denture release apparatus and method of use which is quick and easy to use. Method steps enabling the accomplishment of this object include resting a wearer's chin on the chin rest, inserting the hook into the notch, and opening the wearer's mouth, thus pulling the upper denture off the wearer's upper gum. An advantage associated with the realization of this object is virtually effortless removal of a top denture.

It is yet another object of this invention to provide an upper denture release apparatus and method of use which is economical to produce. Design features allowing this object to be achieved include the use of components and materials which are readily available. Benefits associated with reaching this objective include reduced cost, and hence increased availability.

BRIEF DESCRIPTION OF THE DRAWINGS

The invention, together with the other objects, features, aspects and advantages thereof will be more clearly understood from the following in conjunction with the accompanying drawings.

Six sheets of drawings are provided. Sheet one contains FIGS. 1 and 2. Sheet two contains FIGS. 3 and 4. Sheet three contains FIGS. 5 and 6. Sheet four contains FIGS. 7 and 8. Sheet five contains FIGS. 9 and 10. Sheet six contains FIG. 11.

FIG. 3 is a top view of a denture puller.

FIG. 4 is a left quarter front isometric view of a denture puller.

DETAILED DESCRIPTION OF THE PREFERRED EMBODIMENT

Figure 1:
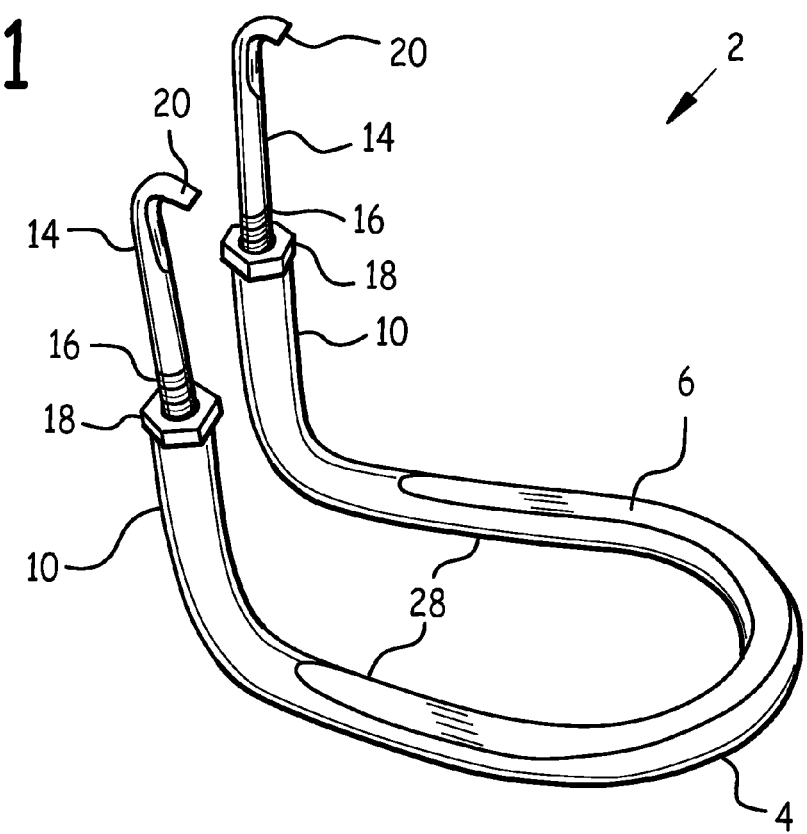
FIG. 1 is a right quarter side isometric view of a denture puller.
Figure 2:
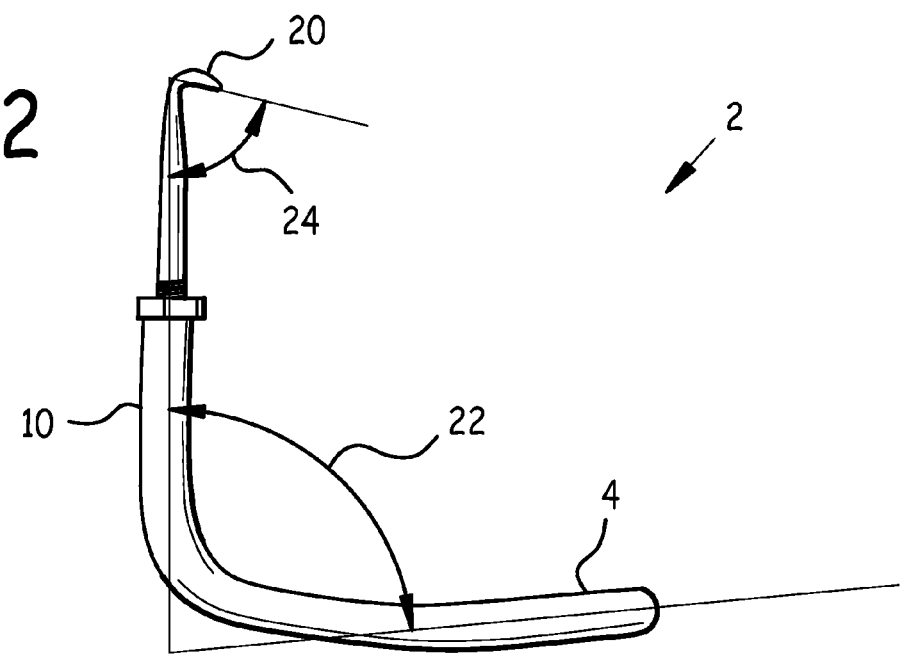
FIG. 2 is a right side view of a denture puller.

Referring now to FIG. 1, a right quarter side isometric view of denture puller 2, and FIG. 2, a right side view of denture puller 2, we may observe that denture puller 2 includes arms 10 rigidly attached to legs 28 at arm angle 22. Chin rest 4 is attached to an end of legs 28 opposite arms 10, and hook 20 is attached to an end of each arm 10 opposite legs 28. Chin rest 4 may be flattened at its upper surface to form chin rest land 6, upon which the chin of a wearer will rest, in order to make the use of denture puller 2 more comfortable to the wearer.

Denture puller 2 engages with notch(es) 82 in upper denture 80 to remove upper denture 80, as is illustrated in FIGS. 7-10. In order to securely engage denture puller 2 with notch 82, it was experimentally determined that a hook declination angle 24 of 75 degrees±15 degrees was optimal. Hook declination angle 24 is the angle between hook 20 and arm 10 when denture puller 2 is viewed from the side, as shown in FIG. 2.

Figure 9:
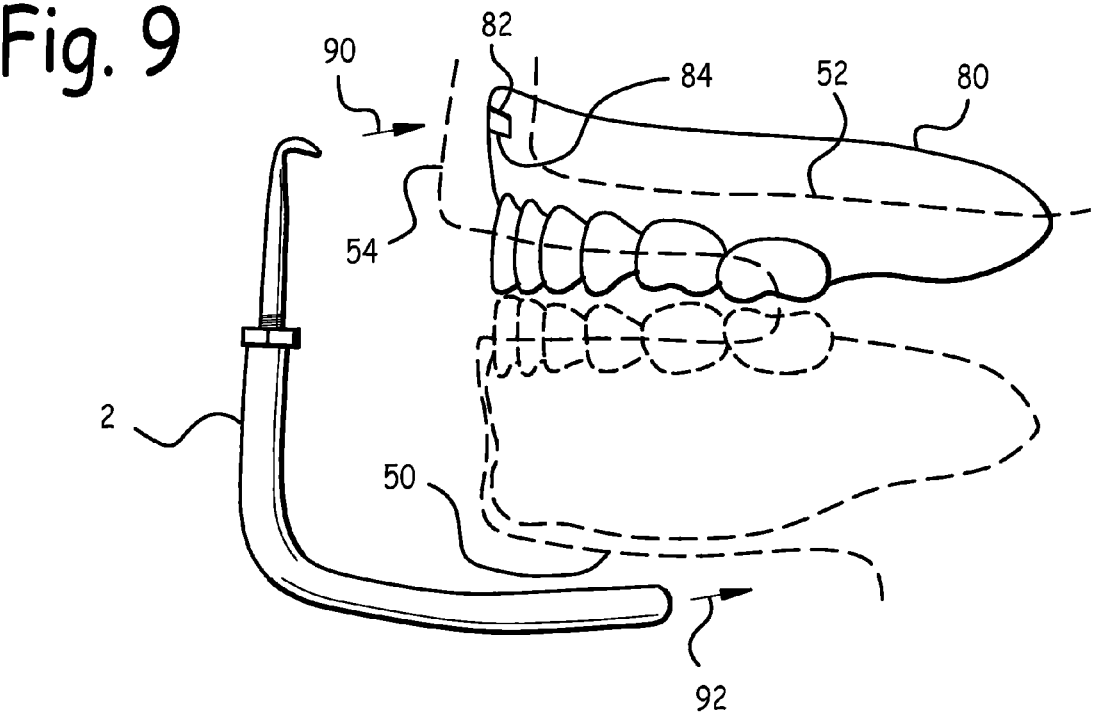
FIG. 9 is a side view of an upper denture in place on a wearer's upper gum, and an upper denture puller about to be emplaced.
Figure 10:
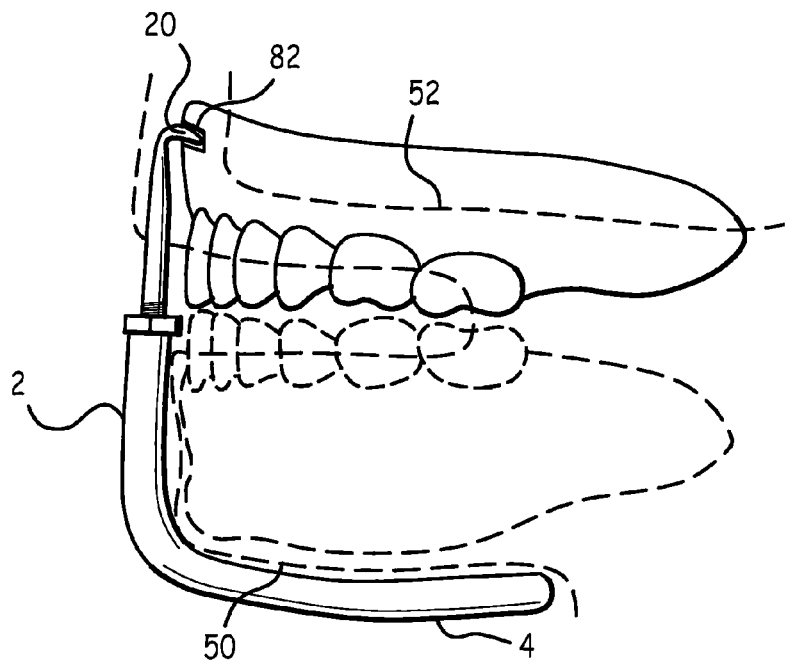
FIG. 10 is a side view of an upper denture in place on a wearer's upper gum, and an upper denture puller emplaced with a hook inserted into a corresponding upper denture notch, and its chin rest in place below the wearer's chin.
Figure 11:
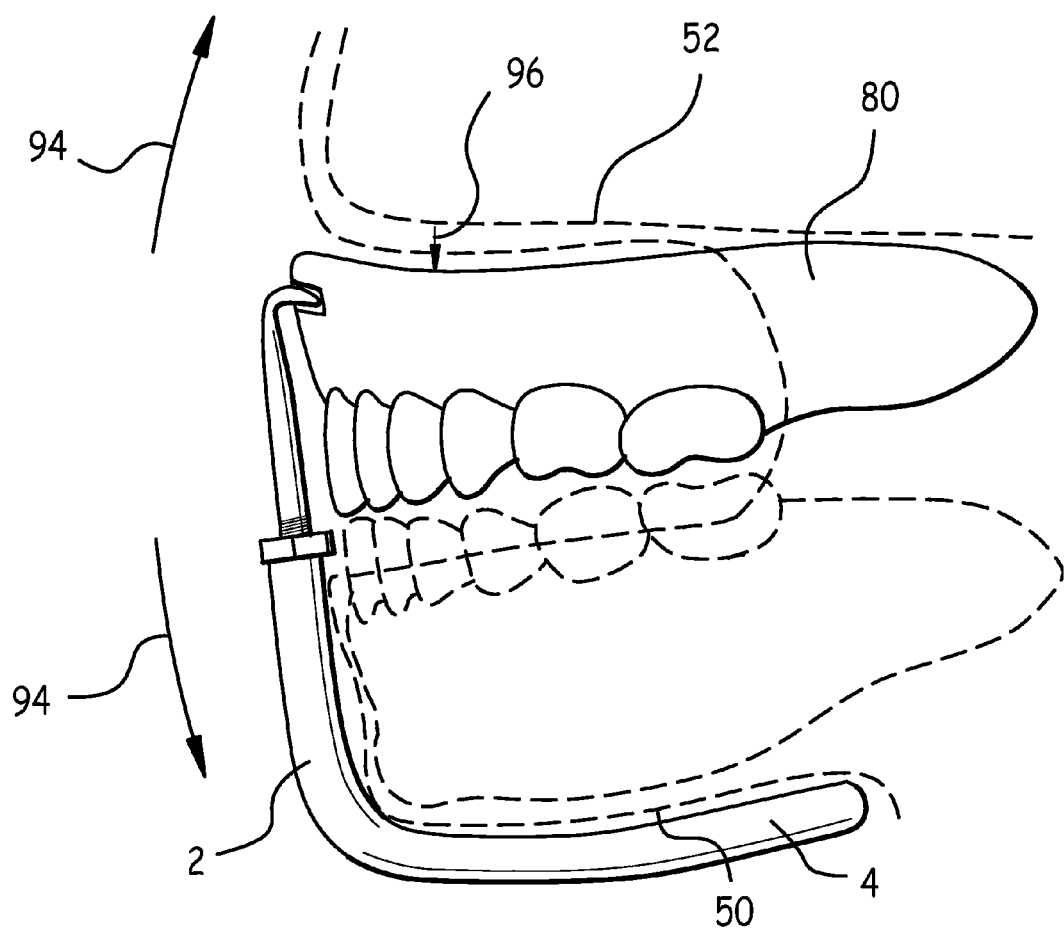
FIG. 11 is a side view of an upper denture puller which has pulled an upper denture off the wearer's upper gum, by the simple motion of the wearer opening his or her mouth.

Denture puller 2 also engages the chin 50 of a denture wearer, in order to provide pulling force to remove upper denture 80 from wearer upper gum 52, as shown in FIGS. 9-11. In order to securely engage denture puller 2 with chin 50, it was experimentally determined that an arm angle 22 of 85 degrees±10 degrees was optimal. Arm angle 22 is the angle between arm 10 and chin rest 4 when denture puller 2 is viewed from the side, as shown in FIG. 2.

In the embodiment of denture puller 2 depicted in FIGS. 1-5, denture puller 2 incorporates two hooks 20. In order to securely engage hooks 20 with notches 82, given the curvature of upper denture 80 when viewed from above, it was experimentally determined that a hook toe angle 26 of 20 degrees±15 degrees was optimal. Hook toe angle 26 is the angle between hook 20 and leg 28 when denture puller 2 is viewed from above as shown in FIG. 3.

Figure 5:
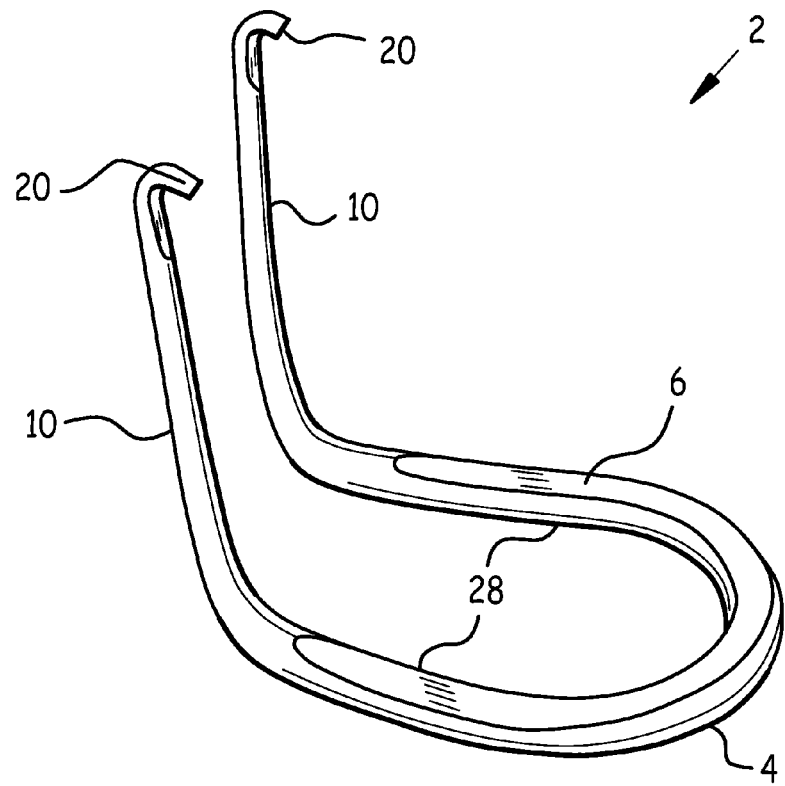
FIG. 5 is a right quarter side isometric view of an alternate embodiment denture puller of one-piece construction.

Denture puller 2 may be of one-piece construction, as illustrated in FIG. 5. In this embodiment, no arm length adjustment means is provided, although it is intended to fall within the scope of this disclosure that the one-piece denture puller 2 depicted in FIG. 5 may optionally incorporate chin rest padding 8. FIG. 4 depicts chin rest padding 8 on chin rest 4, to increase the comfort of a denture wearer using denture puller 2.

In the embodiment of denture puller 2 depicted in FIGS. 1-4, arms 10 incorporate an arm 10 length adjustment means. Referring now also to FIG. 4, a left quarter front isometric view of denture puller 2, the arm length adjustment means is depicted as being an arm threaded bore 12 in an end of each arm 10 opposite leg 28, and arm extension 14 having arm extension thread 16 sized to mate with a respective arm threaded bore 12.

It may be desirable to adjust the length of arm(s) 10 so that denture puller 2 may fit the physiology of different wearers. Adjustment of the length of arm 10 in the preferred embodiment is accomplished by engaging arm extension thread 16 with arm threaded bore 12, rotating arm extension 14 relative to arm 10 until the combined length of arm 10 and arm extension 14 is substantially equal to the distance from the bottom of the wearer's chin 50 to notch 82 in upper denture 80 when the wearer's mouth is closed, and then tightening lock nut 18 onto arm 10 to prevent further rotation of arm extension 14 relative to arm 10. While arm extension thread 16 mating with arm threaded bore 12 is illustrated as a means of arm 10 length adjustment, it is intended to fall within the scope of this disclosure that any appropriate means of arm 10 length adjustment be employed.

Where denture puller 2 incorporates two arms 10, as in FIGS. 1-5, the position of arm extension 14 relative to arm 10 may be further adjusted until hook toe angle 26 is 20 degrees±15 degrees. In the one-piece embodiment depicted in FIG. 5, denture puller 2 may be manufactured such that hook toe angle 26 is 20 degrees±15 degrees.

Figure 6:
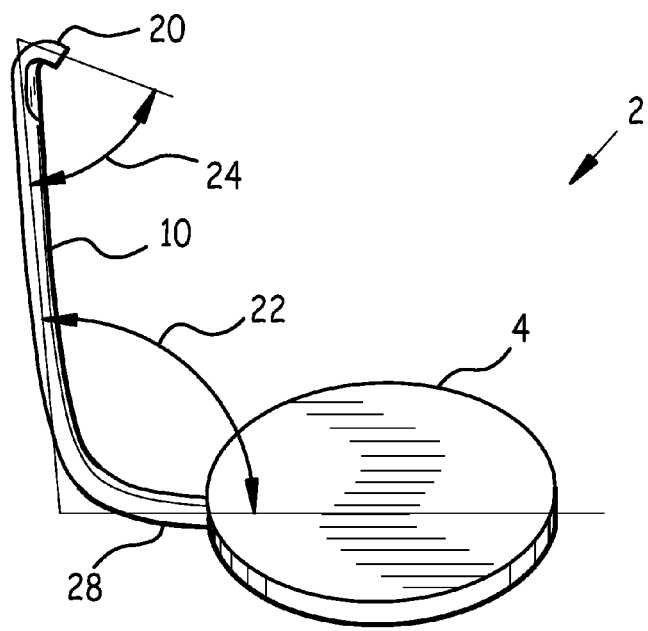
FIG. 6 is a right quarter side isometric view of an alternate embodiment denture puller having a single arm and hook.

FIG. 6 is a right quarter side isometric view of an alternate embodiment denture puller 2 having a single arm 10 and hook 20. In this embodiment, a corresponding upper denture 80 would incorporate a single notch 20 sized and positioned to engage with the single hook 20 in this single-hook embodiment of denture puller 2. The single-hook embodiment of denture puller 2 may incorporate arm length adjustment means as described above, and/or chin rest padding 8. In any of the embodiments disclosed herein arm 10 may be attached directly to chin rest 4.

Although in the embodiment denture puller 2 depicted in FIG. 6 a plan view shape of chin rest 4 is circular, it is intended to fall within the scope of this disclosure that the shape of chin rest 4 be any appropriate shape, including but not limited to polygonal, irregular shaped, kidney shaped, etc. While the figures depict one-arm and two-arm embodiments of denture puller 2, it is intended to fall within the scope of this disclosure that denture puller 2 incorporate any number of arms 10, each with a respective hook 20.

Figure 7:
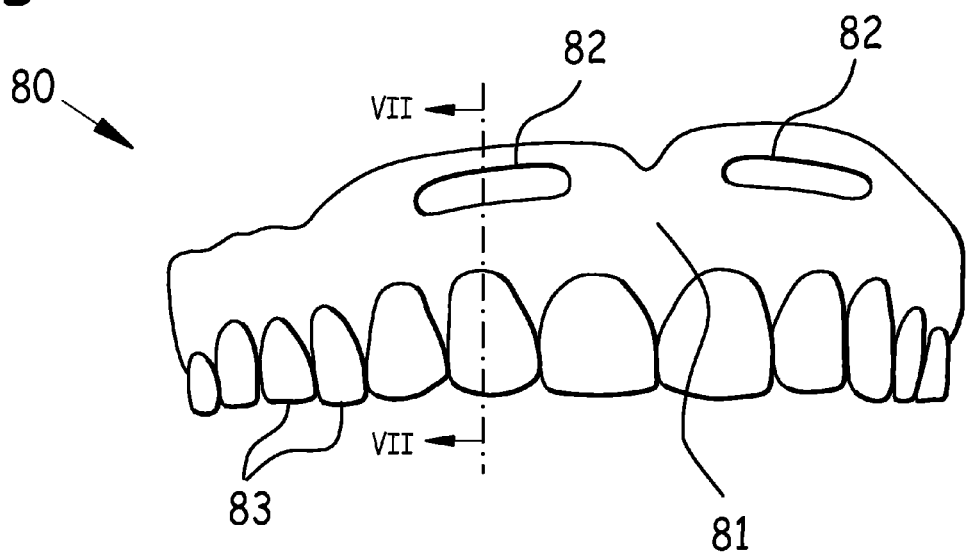
FIG. 7 is a front view of an upper denture having a pair of notches.

FIG. 7 is a front view of upper denture 80 having upper denture teeth 83 secured in upper denture gum 81 in conventional fashion. Upper denture 80 further comprises at least one notch 82, in the preferred embodiment, notch(es) 82 were disposed in upper denture gum 81. In general, upper denture 80 has a notch 82 sized and positioned to admit each hook 20 of a denture puller 2 which will be used to remove upper denture 80.

In the embodiment depicted in FIG. 7, upper denture 80 incorporated two notches 82 sized and positioned to accommodate the hooks 20 of a denture puller 2 having two hooks 20 such as is depicted in FIGS. 1-5.

Figure 8:
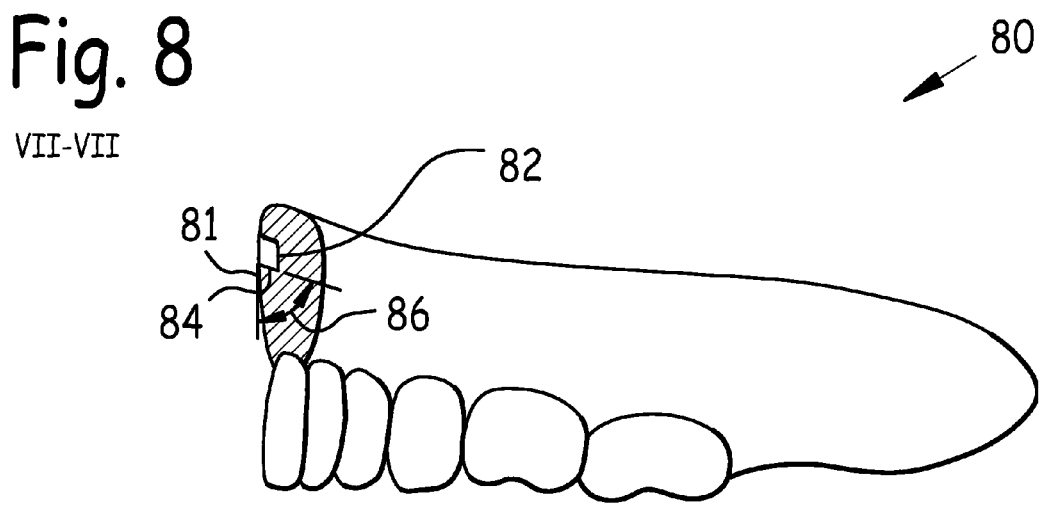
FIG. 8 is a side cross-sectional view of an upper denture, taken at section VII-VII of FIG. 7.

FIG. 8 is a side cross-sectional view of upper denture 80, taken at section VII-VIII of FIG. 7. As may be noted in this figure, notch 82 incorporates notch floor 84. In the preferred embodiment, to provide secure attachment between hook 20 and notch 82, notch floor 84 was disposed at a notch floor angle 86 of 75 degrees±15 degrees to match the preferred embodiment hook declination angle 24 of 75 degrees±15 degrees. Notch floor angle 86 is the angle between notch floor 84 and the upper denture gum 81 adjacent notch floor 84.

FIGS. 9-11 depict the instant method of use of denture puller 2 to remove upper denture 80. FIG. 9 is a side view of upper denture 80 in place on a wearer's upper gum 52, and upper denture puller 2 about to be emplaced.

FIG. 10 is a side view of upper denture 80 in place on a wearer's upper gum 52, and upper denture puller 2 emplaced with hook 20 inserted into corresponding upper denture notch 82, and its chin rest 4 in place below the wearer's chin 50, as indicated by arrows 90 and 92 in FIG. 9. Note hook declination angle 24 matches notch floor angle 86.

FIG. 11 is a side view of denture puller 2 which has pulled upper denture 80 off the wearer's upper gum 52 as indicated by arrow 96, by the simple motion of the wearer opening his or her mouth as indicated by arrows 94 in FIG. 11. In this fashion the strong jaw muscles of the wearer are used to easily overcome the suction and implant post friction fit holding upper denture 80 in place on upper gum 52. After the suction between upper denture 80 and upper gum 52, and the friction fit of any implant posts, have been overcome, denture puller 2 and upper denture 80 may be easily removed from the mouth of the wearer. Implant posts used to hold upper dentures in place are old and well-known in the art, and not shown in the figures in interest of clarity.

Thus, the instant method of use for a denture puller to remove an upper denture includes the steps of:
A. Providing a denture puller having a chin rest attached to a leg, an arm rigidly attached to an end of the leg opposite the chin rest, and a hook attached to an end of the arm opposite the leg;
B. Providing an upper denture installed on a wearer's upper gum, the upper denture having at least one notch sized and positioned to receive the hook when the wearer's chin rests on the chin rest and the wearer's mouth is closed;

C. Resting the wearer's chin on the chin rest, and inserting the hook into the upper denture notch while the wearer's mouth is closed; and
D. Opening the wearer's mouth, whereby the denture puller pulls the upper denture off of the wearer's upper gum.

The instant method may include the further steps of providing arm length adjustment means, and adjusting the length of the arm so that the arm length is substantially equal to the distance between the wearer's chin and the upper denture notch when the wearer's mouth is closed.

The instant method may include the further steps of attaching the arm to the leg at an arm angle 22 of 85 degrees±10 degrees when the denture puller is viewed from the side.

The instant method may include the further steps of attaching the hook to the arm at a hook declination angle of 75 degrees±15 degrees when the denture puller is viewed from the side.

The instant method may include the further steps of providing a notch floor in the notch, the notch floor being disposed at a notch floor angle of 75 degrees±15 degrees when the upper denture is viewed from the side.

The instant method may include the further steps of attaching the hook to the arm at a hook toe angle of 20 degrees±15 degrees when the denture puller is viewed from above.

In the preferred embodiment denture puller 2 was made of metal, stainless steel, synthetic, nylon, plastic, or any other appropriate material. Chin rest padding 8 was made of synthetic, foam rubber, plastic, or any other appropriate material.

In the preferred embodiment, notches 82 were disposed high enough on upper denture gum 81 so as to be hidden behind the upper lip 54 of the wearer.

While a preferred embodiment of the invention has been illustrated herein, it is to be understood that changes and variations may be made by those skilled in the art without departing from the spirit of the appending claims.

DRAWING ITEM INDEX

2 denture puller
4 chin rest
6 chin rest land
8 chin rest padding
10 arm
12 arm threaded bore
14 arm extension
16 arm extension thread
18 lock nut
20 hook
22 arm angle
24 hook declination angle
26 hook toe angle
28 leg
50 chin
52 upper gum
54 upper lip
80 upper denture
81 upper denture gum
82 notch
83 upper denture teeth
84 notch floor
86 notch floor angle
90 arrow
92 arrow
94 arrow
96 arrow

I claim:

1. A method of use for an upper denture release apparatus comprising the steps of:
    A. Providing a denture puller having a chin rest attached to an arm, and a hook attached to an end of said arm opposite said chin rest;
    B. Providing an upper denture installed on a wearer's upper gum, said upper denture having at least one notch sized and positioned to receive said hook when said wearer's chin rests on said chin rest and said wearer's mouth is closed;
    C. Resting said wearer's chin on said chin rest, and inserting said hook into a corresponding said upper denture notch while said wearer's mouth is closed; and
    D. Opening said wearer's mouth, whereby said denture puller pulls said upper denture off of said wearer's upper gum.

2. The method of claim 1 comprising the further step of providing arm length adjustment means, and adjusting a length of said arm so that said arm length substantially equals a distance between said wearer's chin and said upper denture notch when said wearer's mouth is closed.

3. The method of claim 1 comprising the further step of attaching said arm to said chin rest at an arm angle of 85 degrees±10 degrees when said denture puller is viewed from the side.

4. The method of claim 1 comprising the further step of attaching said hook to said arm at a hook declination angle of 75 degrees±15 degrees when said denture puller is viewed from the side.

5. The method of claim 4 comprising the further step of providing a notch floor in said notch, said notch floor being disposed at a notch floor angle of 75 degrees±15 degrees relative to said upper denture gum adjacent said notch when said upper denture is viewed from the side.

6. The method of claim 1 comprising the further steps of providing two legs rigidly attached to said chin rest, rigidly attaching one said arm to an end of each said leg opposite said chin rest, and attaching each said hook to and end of a respective said arm at a hook toe angle of 20 degrees±15 degrees relative to a respective said leg when said denture puller is viewed from above.

\* \* \* \* \*